United States Patent
Schaldach et al.

(10) Patent No.: US 6,219,581 B1
(45) Date of Patent: Apr. 17, 2001

(54) PACING LEAD SYSTEM

(75) Inventors: Max Schaldach, Erlangen (DE); Tran Thong, Lake Oswego, OR (US)

(73) Assignee: Biotronik Mess-und Therapiegeraete GmbH & Co. Ingenieurbuero Berlin, Berlin (DE)

(*) Notice: Subject to any disclaimer, the term of this patent is extended or adjusted under 35 U.S.C. 154(b) by 0 days.

(21) Appl. No.: 09/125,366

(22) PCT Filed: Dec. 17, 1997

(86) PCT No.: PCT/DE97/03024

§ 371 Date: Aug. 17, 1998

§ 102(e) Date: Aug. 17, 1998

(87) PCT Pub. No.: WO98/26836

PCT Pub. Date: Jun. 25, 1998

(30) Foreign Application Priority Data

Dec. 17, 1996 (DE) .............................. 196 54 491

(51) Int. Cl.[7] ........................................... A61N 1/05
(52) U.S. Cl. .................. 607/122; 607/119; 607/129; 607/9
(58) Field of Search ...................... 607/122, 121, 607/123, 126, 128, 9, 4, 129

(56) References Cited

U.S. PATENT DOCUMENTS

| | | |
|---|---|---|
| 3,915,174 | 10/1975 | Preston . |
| 4,394,866 | 7/1983 | Hughs . |
| 4,444,195 * | 4/1984 | Gold ..................................... 600/374 |
| 4,796,642 * | 1/1989 | Harris ................................... 600/585 |
| 5,235,977 | 8/1993 | Hirschberg et al. . |
| 5,314,430 | 5/1994 | Brady . |
| 5,376,103 | 12/1994 | Anderson et al. . |
| 5,571,158 * | 11/1996 | Bolz et al. ............................. 607/121 |
| 5,628,779 * | 5/1997 | Bornzin et al. ....................... 607/123 |
| 5,662,698 * | 9/1997 | Altman et al. ........................ 607/123 |
| 5,709,644 * | 1/1998 | Bush ..................................... 607/116 |
| 5,728,140 * | 3/1998 | Salo et al. ................................. 607/9 |
| 5,824,030 * | 10/1998 | Yang et al. ........................... 607/122 |

FOREIGN PATENT DOCUMENTS

| | | |
|---|---|---|
| 33 00 672A1 | 7/1984 | (DE) . |
| 19507929A1 | 9/1996 | (DE) . |
| 19609471A1 | 11/1997 | (DE) . |
| 05 59 933A1 | 9/1993 | (EP) . |
| 0601338A1 | 6/1994 | (EP) . |
| 060 688 A2 | 7/1994 | (EP) . |
| 0677301A1 | 10/1995 | (EP) . |
| WO 97/31678 | 9/1997 | (WO) . |

OTHER PUBLICATIONS

R. Frolich et al.; Measurement and Analysis of Monophais Action etc.; Jun. 30, 1995; Biomed. Technik 40(1995), pp. 154–159.

* cited by examiner

*Primary Examiner*—Kennedy Schaetzle
(74) *Attorney, Agent, or Firm*—Venable; George H. Spencer; Robert Kinberg

(57) ABSTRACT

A pacing electrode arrangement for stimulating the heart by means of an implantable pacemaker, comprising a first pacing electrode arranged in the vena cava superior and a second pacing electrode arranged in either the atrium, or a blood vessel near the heart other than the vena cava superior, or arranged at a distance from the heart, whereby the first and the second pacing electrode essentially enclose between them a predetermined, central region of the cardiac stimulus generating and conduction system.

20 Claims, 4 Drawing Sheets

PACING LEAD SYSTEM

BACKGROUND OF THE INVENTION

The invention relates to a pacing electrode arrangement for a pacemaker.

Implanted pacemakers in connection with pacing electrodes, arranged on an intracardiac electrode catheter and positioned on the heart inside wall, have long been used for the treatment of various chronic arrhythmias. They are designed to stimulate the excitable cardiac tissue, thereby compensating defects in the body's own cardiac stimulus generating and conduction system.

The designs for pacemaker and associated electrodes have been improved more and more. Numerous technical solutions for attaching the electrode leads to the heart wall—in the ventricle as well as the atrium—have been discovered and essential practical improvements have actually been made, with the goal of ensuring good, long-term contact between the pacing electrode(s) and the heart tissue, so as to achieve simultaneously an energy-saving and secure stimulation.

Nevertheless, the dislocation of electrodes is still considered one of the most serious complications encountered in pacemaker therapy, which results in a worsening or a loss of contact with the heart to be stimulated on the inside wall and consequently increases the stimulus threshold considerably, thus leading to an increased current consumption of the pacemaker as well as a reduced life expectancy and, in the worst case, to the operational failure of this pacemaker. The technical development of attachment mechanisms (becoming ever more complicated and expensive) therefore still continues.

In addition to high production costs, these traditional electrode arrangements have the disadvantage of requiring a great deal of experience and expenditure for the implantation.

Also known are electrode arrangements, which are not intended for a permanent attachment in the ventricle or the atrium (so-called "floating" arrangements) and are easier to implant, are cheaper and require less knowledge for the implantation. These electrode arrangements are known primarily from implantable defibrillator arrangements, but are also used with pacemakers.

An early arrangement of this type is disclosed in the U.S. Pat. No. 3,915,714.

The European Patent Application EP 0 601 338 A1 describes an electrode system for an implanted defibrillator, comprising at least two intravascular positioned coil electrodes (spiral-type electrodes), held in place without special fasteners, simply because of their size. One of these large-surface defibrillation electrodes can be arranged specifically in the vena cava superior.

The European Patent Application EP-O 677 301-A1 discloses an electrode catheter for use with a defibrillator, which comprises an elongated, cylindrical electrode with a covering that can be moved along the electrode lead, thereby permitting a displacement of the effective electrode region. For example, the catheter can be adjusted such that a first electrode is positioned in the ventricle and that the electrode region, positioned through movement of the covering, is located in the vena cava superior.

In past clinical experiments, pacing electrodes that float in the heart could not ensure with sufficient certainty a reliable stimulation, given the available stimulus pulse voltage and making economic use of the limited battery capacity, to allow for a worthwhile practical operation.

Apart from the aforementioned practical problems, the traditional method of transmitting the stimulation pulses from an implanted pacemaker via electrodes installed in the wall to the excitable muscle tissue of the heart inside wall, in the lower region of the ventricle or the atrium, cannot lead to satisfactory results in a number of frequently occurring arrhythmias, owing to basic physiological considerations. This procedure is designed to stimulate regions in the lower hierarchical planes of the cardiac stimulus generating and conduction system. The procedure can require, for example, a technically involved two-chamber stimulation (in the atrium and ventricle), even for clinical pictures shaped by a sinus node defect, but where the remaining stimulus conduction system is for the most part intact.

The applicant's DE Patent Application 196 09 471.2 relates to an arrangement with preferably floating pacing electrodes of varied polarity, designed to produce a stimulus pulse field that is "focused" onto predetermined heart tissue regions.

SUMMARY OF THE INVENTION

It is the object of the invention to specify an improved electrode arrangement of the aforementioned generic type, which permits a pacemaker operation that is more reliable and better follows the physiological conditions with respect to the stimulus pulse localization, and which is easier to produce and can be positioned easily and safely.

This object is solved with a pacing electrode arrangement for stimulating the heart by means of an implantable pacemaker, comprising a first pacing electrode that is arranged in the vena cava superior and a second pacing electrode, arranged in the atrium or a vessel near the heart other than the vena cava superior, or arranged at a distance to the heart, such that the first and the second pacing electrode essentially enclose between them a predetermined, central region of the cardiac stimulus generating and conduction system, in particular the sinus node.

The invention comprises the idea of realizing an electrode arrangement for conducting the pacemaker stimulation pulses to the highest regions of the cardiac stimulus generating and conduction system—primarily the sinus node—so that a sinus node defect, for example, can be compensated easily by means of a precisely localized electric stimulation at the location of the defect.

In order to realize this idea, the suggested electrode arrangement uses a localization of the stimulus pulse field, generated from a single stimulation voltage, in the sinus node or any other central region of the stimulus generating system. The pacing electrodes used for this are arranged in blood vessels near the heart and optionally in the atrium, directly adjacent to this region (preferably without being secured there).

At least the first pacing electrode in the blood vessel near the heart is preferably arranged on an electrode lead that extends at least into the atrium and is designed to be placed without being secured, in particular to be floating.

In one preferred modification of this embodiment, the second pacing electrode is arranged on the electrode lead at such a distance to the first pacing electrode that it is positioned in the atrium following implantation.

The electrode lead furthermore can comprise one or even several electrode(s) that is (are) distally spaced apart from the first or second pacing electrode in such a way that the electrode(s) is (are) arranged in the ventricle after implantation. This (these) ventricle electrode(s) can function in particular as sensing electrode(s) for special arrhythmias—e.g. a complete AV block—but also as additional pacing electrode(s).

The first pacing electrode—or the electrode lead, if such is provided—in particular can have positioning means to adjust the predetermined position of the first pacing electrode in the vena cava superior and/or the second pacing electrode in the atrium.

To be specific, the first pacing electrode itself can be shaped in such a way that it occupies a predetermined position in the vena cava superior after implantation or, if necessary, also provides the atrium electrode with a predetermined position—insofar as it is mechanically connected to it in the embodiment having a joint electrode lead. This can be achieved, for example with a spiral design or a design containing a spiral segment, for which the spiral diameter approximately corresponds to the vessel inside diameter.

It is useful if the aforementioned positioning means is (are) designed as integral part(s) of the electrode lead and, in an embodiment with multiple adjustment options, comprise means for adjusting a predetermined curvature in the electrode lead after it is implanted.

As alternative or in addition to that, the positioning means can comprise electrically insulating spacers or spacers that are insulated against the pacing electrodes.

For a subsequent correction of the electrode position with respect to the heart tissue region to be stimulated, these positioning means can furthermore include means that can be actuated from outside of the body and are designed to change the position of the first and/or second pacing electrode following implantation.

The first and/or the second stimulation electrode have a ring-shaped or ring segment-shaped design with a length/diameter ratio of maximum 2, preferably less than 1, depending on their stimulation function. (This characterization also includes a nearly cylinder-shaped or "pot"-shaped point electrode design of the first or second electrode at the distal end of a feed line.)

The first and/or second pacing electrode furthermore has a preferably geometric surface of less than 10 mm$^2$ and in particular a fractal surface microstructure for enlarging the electrically effective surface by a factor of at least $10^2$.

For an especially variable embodiment with respect to the achievable stimulus pulse field distribution, an indifferent surface electrode is provided outside of the heart as additional pacing electrode. This indifferent surface electrode can be realized in particular as a part of the pacemaker housing.

The precise localization of a sufficiently large potential gradient through the claimed electrode arrangement makes it possible to exceed the stimulation threshold in tissue regions that do not make direct contact with the electrodes and thus the stimulation of target regions for excitation, which are not located on the cardiac wall surface and additionally are located in heart regions where an active securing of electrodes is practically impossible, that is to say the sinus node region or maybe the atrioventricular (AV) node region or other hierarchically relatively high-level regions of the stimulus generating and conduction system.

Since it is not necessary to secure the electrode lead for the suggested pacing electrode arrangement on the cardiac wall, it can "swim" in the heart. Consequently, it is useful if this pacing electrode arrangement is constructed with enough flexural strength and, if necessary, is provided it with such a curvature in the longitudinal extension that the electrodes do not make direct contact with the vessel wall or atrium wall after being inserted, but are arranged near the region to be stimulated.

The curvature or the outward projection of the spacers on the electrode lead are achieved through suitable (and as such known) means after the insertion, preferably with elements made of a memory alloy, activated by the body temperature, or by prestressed elements that take on a pre-molded form when a guide wire, used for the insertion, is removed from the electrode lead. It is also possible to provide means for changing the curvature from the outside, e.g. a reinforcement wire that is effective in the manner of a guide wire.

In another advantageous embodiment, varied electrode regions, arranged either on the electrode lead or formed by the pacemaker housing, can be activated simultaneously or alternately to permit a varied field distribution, in particular also through a remote-controlled, programmed switching. Different physiological requirements can be met in this way. Nevertheless, only two (internal or external) stimulator connecting leads are necessary for the atrium.

Advantageous modifications of the invention are characterized in the dependent claims or are shown in further details in the following text with the aid of the figures and together with the description of the preferred embodiment of the invention.

DETAILED DESCRIPTION OF THE INVENTION

Figure 1:
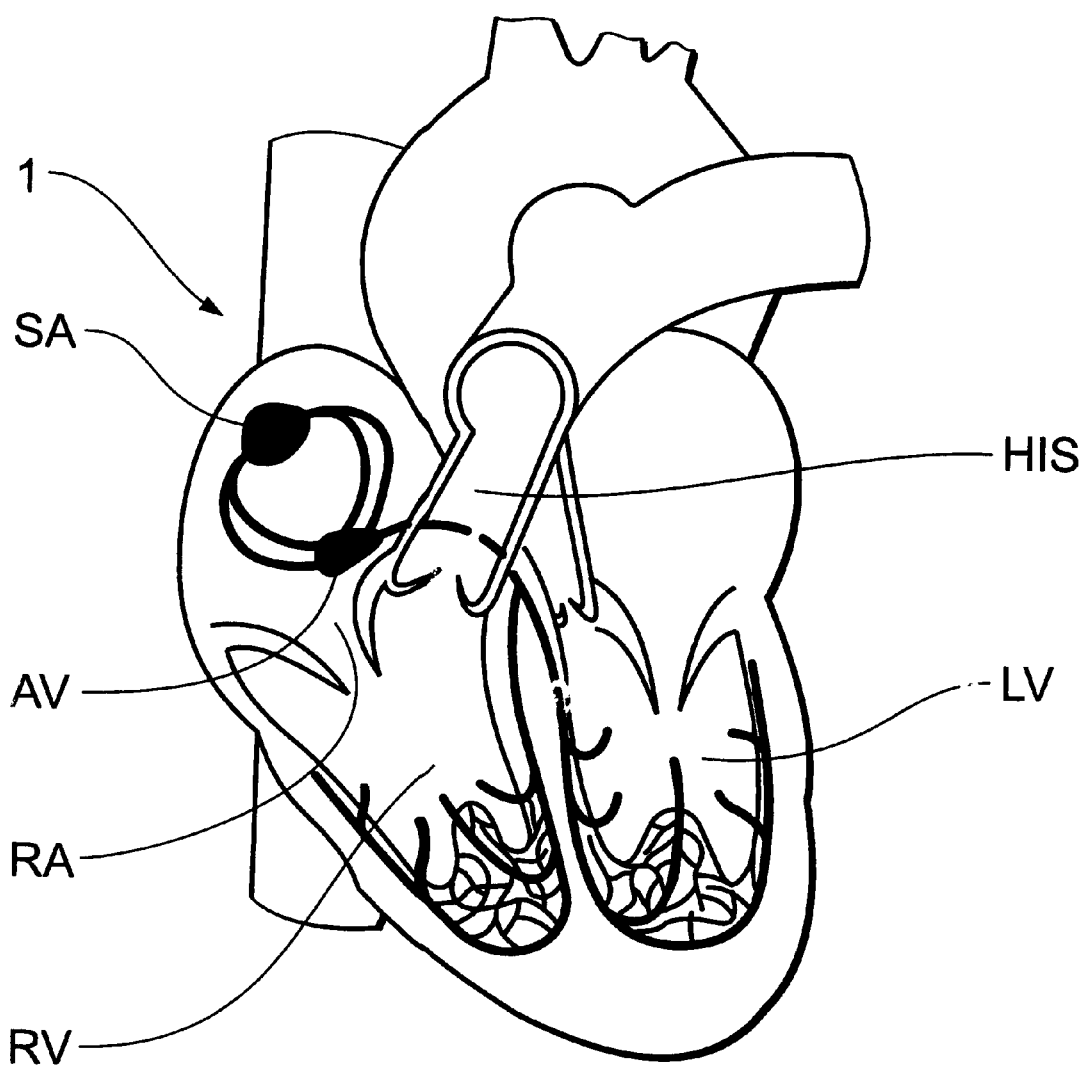
FIG. 1 A schematic illustration of the stimulus generating and conduction system of the heart.

The position of the stimulus generating and conduction system elements inside the heart 1, which also include the His' bundle not mentioned in the above and the left or right branch ("left" or "right bundle branch") that respectively ends in the Purkinje fibers is shown initially as a sketch in FIG. 1. It shows that only peripheral regions of the system can be stimulated with the standard stimulation method via electrodes anchored in the wall in the lower regions of the ventricle (left ventricle (LV) or right ventricle (RV)) and/or in the atrium (RA)), so that it is not possible to have a direct effect on defects in the central regions, e.g. the sinus node (SA) or AV nodes (AV).

Selected examples of concrete pacing electrode arrangements as described below, make use of the basic idea behind the invention, but should not be understood as limiting it. The person skilled in the art can arrive without problems at a plurality of additional configurations, simply by reverting to details of known electrode leads, which also fall within the scope of protection as stated in the claims.

Figure 2:
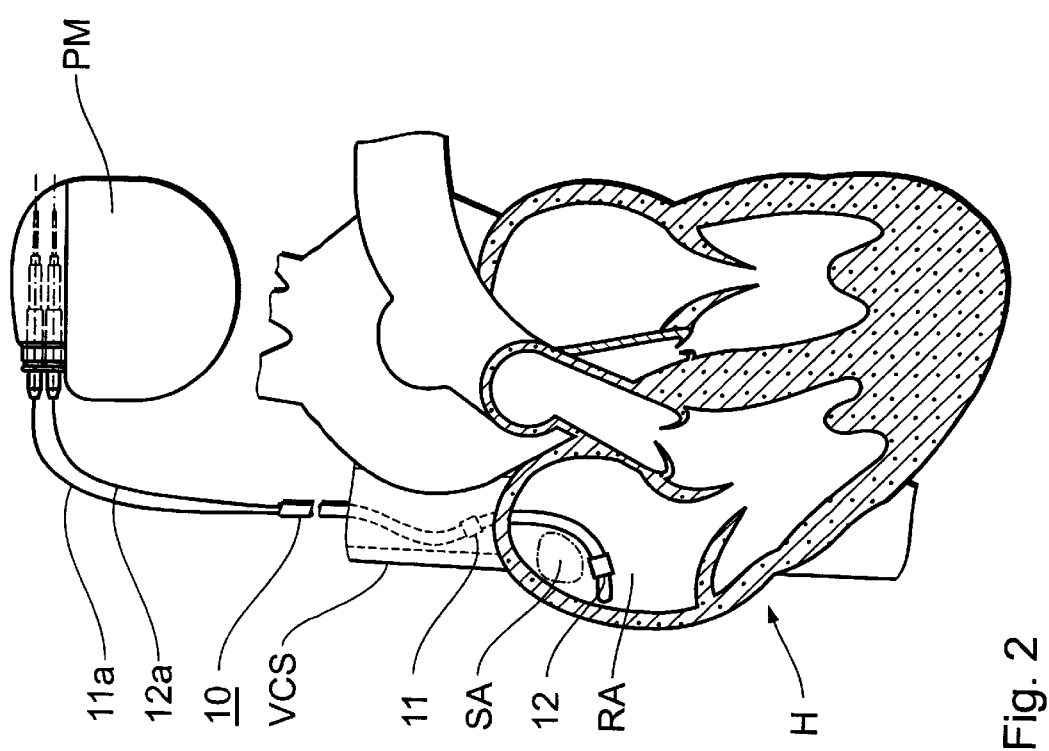
FIG. 2 A schematic illustration of a pacing electrode arrangement according to one embodiment of the invention.

FIG. 2 is a schematic illustration of an electrode lead 10, curved into a S shape and placed via the vena cava superior VCS into the right atrium RA of heart H, such that it floats. A first pacing electrode 11, positioned as shown in the vena cava following implantation, and a second pacing electrode 12, positioned in the high atrium at a slight distance to the distal lead end, are formed on lead 10. Both electrodes 11, 12 are designed as ring electrodes (not discernible in the Figure) with fractal-type microstructured surface. For the insertion, the lead body with preshaped curvature is stretched in the known way by a guide wire (not shown) and is turned during the implantation to an angle position, so as to make it possible for the electrodes to enclose the sinus node SA essentially between them and with the least possible distance. For a bipolar operation, the electrodes 11, 12 are connected via feed lines 11a, 12a to a pacemaker PM and stimulate the sinus node SA directly if a stimulation pulse is emitted at the pacemaker exits.

Figure 3:
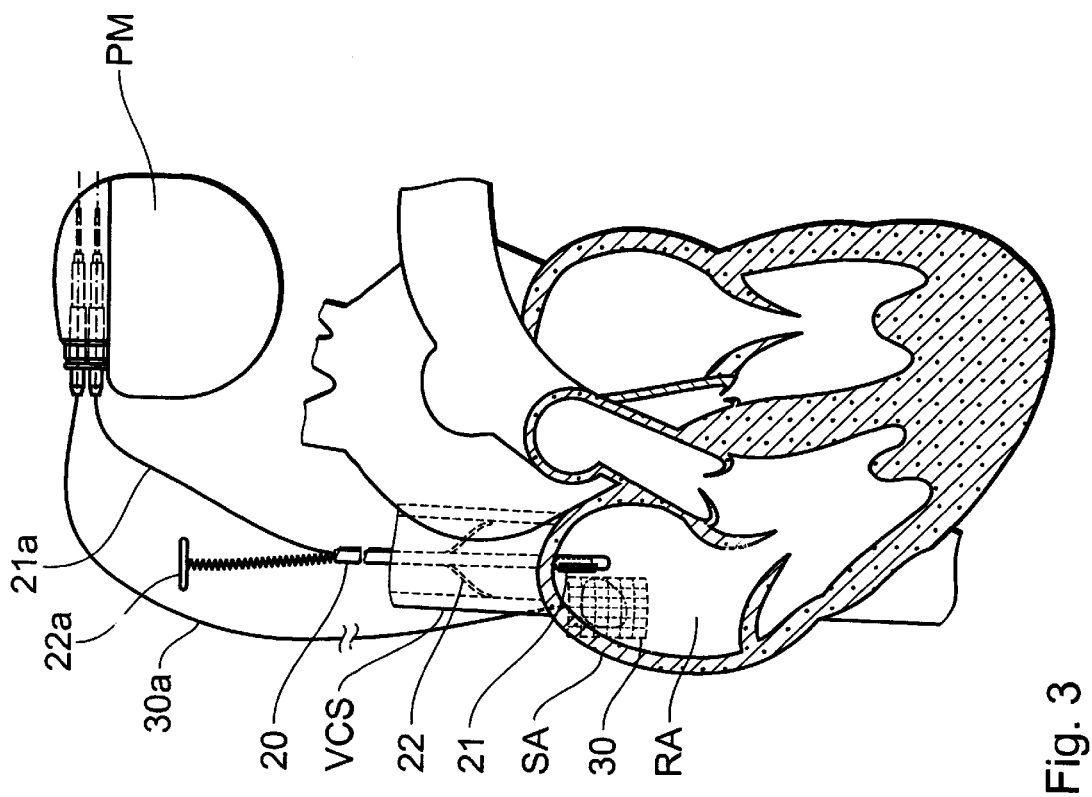
FIG. 3 A schematic illustration of a pacing electrode arrangement according to a second embodiment of the invention.

FIG. 3 is a respective illustration of an electrode lead 20, the distal end of which extends into the transition region between vena cava superior VCS and the right atrium RA and which comprises at its distal end an electrode 21 with semicircular cross section. This electrode is connected via a feed line 21a to one pole of a pacemaker PM while a relatively small surface electrode 30, implanted extra-cardiac but near the sinus node SA, is connected to the other output. (Depending on the patient-specific position of the sinus node, an insertion of the second electrode into a vessel near the heart may be possible and is preferable since this reduces the expenditure for the operation.) The position of lead 20 and the first electrode 21 in the vessel VCS and thus the position relative to the sinus node SA is adjusted with spacers 22, the outward projection of which can be controlled from the outside via an actuation lever 22a. A stimulus pulse field that penetrates the sinus node is also formed in this arrangement if a stimulus pulse is emitted by the pacemaker PM, provided the electrodes 21, 30 are positioned correctly.

By omitting the extra-cardiac electrode 30, it is on principle possible to carry out a unipolar reference stimulation against the pacemaker PM housing with the aid of electrode lead 20, shown in FIG. 3, which reduces the technical and operative expenditure at the cost of a tendency to higher energy consumption and somewhat increased susceptance to trouble. Furthermore, with the pacemaker housing as reference electrode, the bipolar arrangements in FIGS. 2 and 3 can be supplemented to form tripolar pacing arrangements, thereby permitting a further improved control of the field distribution.

Figure 4:
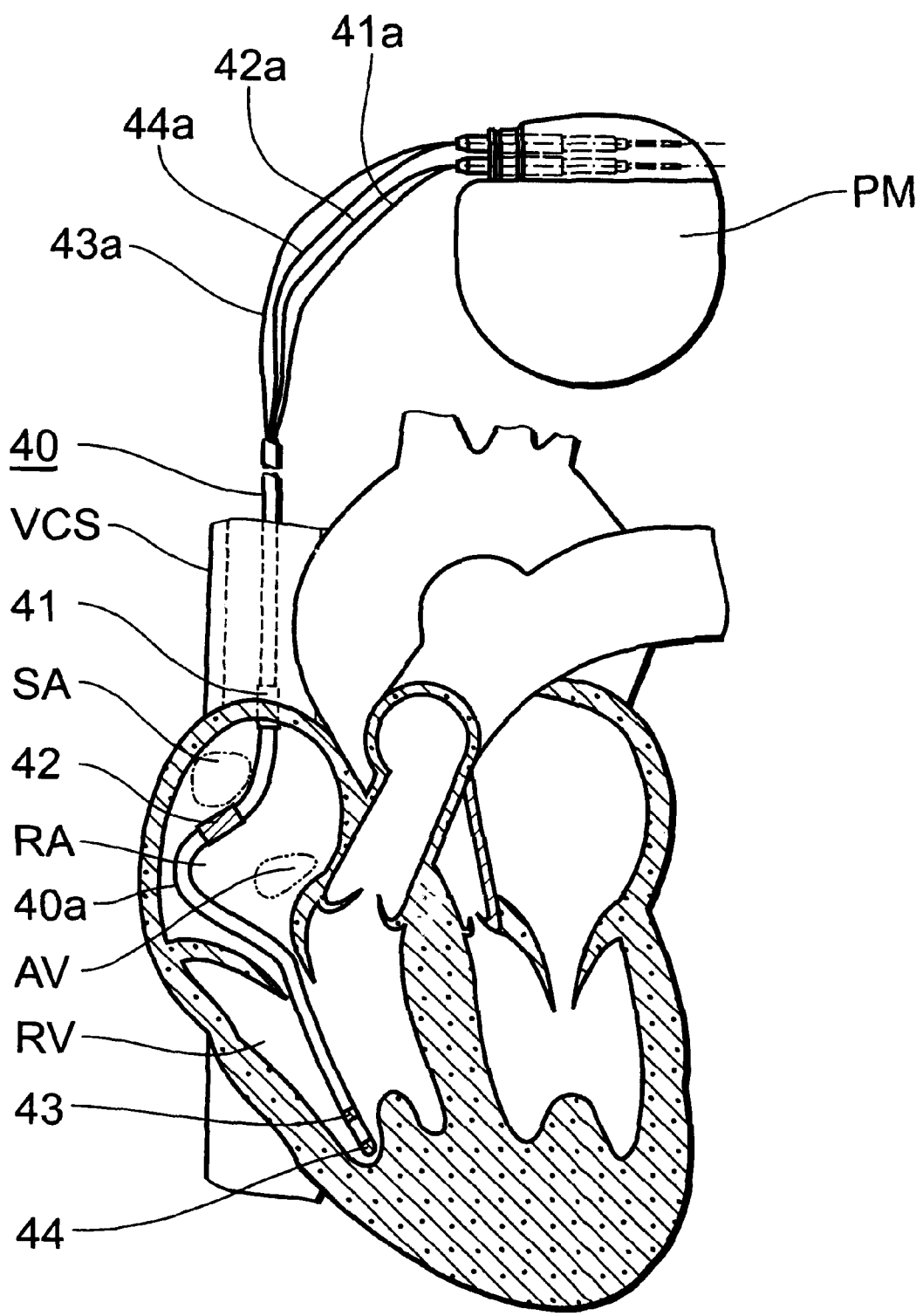
FIG. 4 A schematic illustration of a pacing electrode arrangement according to a third embodiment of the invention, as well as FIG. 5 A schematic illustration of a pacing electrode arrangement according to a fourth embodiment of the invention.

FIG. 4 shows a schematic illustration of a third embodiment, having an electrode lead 40 that extends into the apex of the right ventricle RV and comprising a total of four electrodes 41 to 44 with the respective feed lines 41a to 44a. The proximal electrode pair 41, 42, which is positioned in the vena cava superior VCS or in the right atrium RA following implantation of the lead—as can be seen in the FIG. 4—again functions to directly stimulate the sinus node SA. A stabilization of the position of electrodes 41, 42 without actually securing them to the cardiac wall is achieved by bending the lead 40a at a predetermined distance to the distal end, e.g. realized in the known way by using (not shown) electrode lead components made of a memory alloy.

The point electrode 44, arranged on the distal lead end, and the ring electrode 43, spaced apart from this point electrode by several millimeters up to approximately 2 cm, both of which are positioned in the ventricle RV following implantation are used in a manner known per se for a bipolar detection of the chamber actions for controlling the pacemaker PM and, if necessary, for an additional stimulation in the ventricle, e.g. for patients with complete AV block where the stimulus pulses transmitted to the sinus node are not transmitted to the ventricle.

It is obvious that the effect intended with the invention can also be achieved with groups composed of several electrodes. Thus, two or more electrodes can also be arranged in the atrium or an additional electrode can be located in the vena cava superior. The use of one or the other electrode arrangement can depend on the actual position of the sinus node in a patient and can depend on the patient's stimulation threshold.

Figure 5:
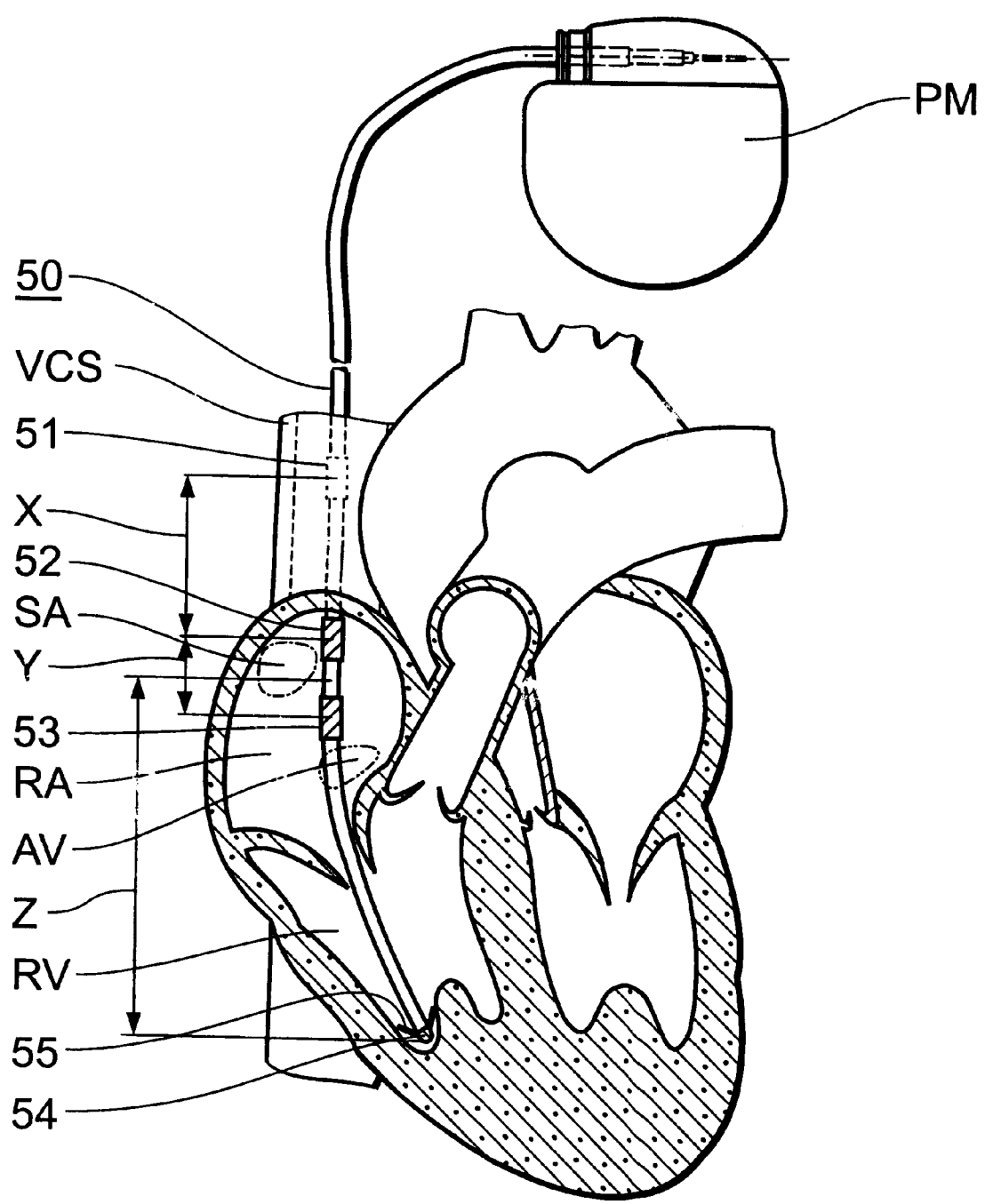

FIG. 5 shows a schematic illustration of such a fourth embodiment, for which an electrode lead 50 that extends into the apex of the right ventricle RV comprises on the whole four electrodes 51 to 54 with a feed line 50, wherein the individual leads for the individual electrodes are not shown in further detail here since they are anyway provided inside the joint line 50. The proximal electrode pair 51, 52 or 53, which is positioned in the vena cava superior VCS or the right atrium RA following implantation—as can be seen in the FIG. 5—again functions to directly stimulate the sinus node SA. With a bipolar stimulation, the electrodes 52 and 53 in this case can be used alternatively as counter electrode for 51, wherein the pacemaker PM housing can also be included in the stimulation. The ventricle electrode 54, which is provided with fastening means in the form of tines 55 is connected unipolar to the pacemaker PM housing as counter electrode.

The following table shows various connecting options, wherein the two pacemaker connections for atrium and ventricle stimulation or sensing are respectively given the references A1 and A2 and V1 and V2 in the lines. The ventricle electrode in the illustrated example is constantly connected as unipolar electrode, whereas the ring electrodes 52 and 53, positioned in the atrium region, can alternatively be operated bipolar, together with the vena cava electrode 51 (columns A and B in the table). In C, one of the ring electrodes 53 is unipolar counter-connected to the pacemaker PM housing. In D, one of the electrodes 51 is counter-connected to the additional electrode 52, which in turn is connected to the pacemaker PM housing. In column E, two of the electrodes 51 and 52 are jointly counter-connected to the pacemaker housing. In column F, two of the electrodes 51 and 52 are jointly counter-connected to the pacemaker housing, which in turn is connected jointly with one of the electrodes in this group.

It is preferable if the distance X between the two electrodes 51 (vena cava) and 52 (atrium) is approximately 15 to 20 mm, while the two atrium electrodes 52 and 53 are spaced apart approximately 10 mm (distance Y). The distance Z between the atrium electrodes 52 and 53 and the ventricle electrode 54 is approximately 120 to 140 mm.

It is obvious that a plurality of connecting options are provided in this way for the electrodes in the atrium region. These options have in common that by superimposing the field distribution, generated with several electrodes, it is possible to generate a stimulation effect that can meet different requirements, wherein this respectively results in a concentration of the field lines in specially selected regions. All voltages can here be discharged at the atrium connection. Furthermore, the atrium pacemaker connection for the cases listed in columns C and E requires only a unipolar connection.

|  | A | B | C | D | E | F |
|---|---|---|---|---|---|---|
| V1 | PM | PM | PM | PM | PM | PM |
| V2 | 54 | 54 | 54 | 54 | 54 | 54 |
| A1 | 51 | 51 | PM | 52, PM | 51, 52 | 51, 52 |
| A2 | 53 | 52 | 53 | 51 | PM | PM, 53 |

The point electrode 54, arranged at the distal lead end, and the ring electrode 53, spaced apart from this point electrode by several millimeters up to approximately 2 cm, are used in the known way per se for a bipolar detection of the chamber action for controlling the pacemaker PM and, if necessary, also for additional stimulation in the ventricle, e.g. for patients with complete AV block where the stimulus pulses supplied to the sinus node are not transmitted to the ventricle.

A stimulus pulse field localization in the AV node (compare FIG. 1) or another central region of the stimulus generating and conduction system can be achieved with arrangements that are very similar to those described in the above.

What is claimed is:

1. A pacing electrode arrangement for stimulating the heart by means of an implantable pacemaker (PM), comprising a first vena cava superior pacing electrode for arrangement in the vena cava superior; a second pacing electrode for arrangement in one of (1) the atrium, (2) a vessel near the heart other than the vena cava superior, and (3) at a distance to the heart, not in a vassel near the heart whereby the first and the second pacing electrode essentially enclose between them a predetermined, central region of the cardiac stimulus generating and conduction system; and a positioning means, including an electrically insulating spacer, for adjusting a predetermined position of the first pacing electrode in the vena cava superior.

2. A pacing electrode arrangement according to claim 1, wherein the first pacing electrode is arranged on an electrode lead, which extends at least into the atrium and is designed to be positioned without being secured.

3. A pacing electrode arrangement according to claim 2, wherein the second pacing electrode is arranged at such a distance to the first pacing electrode on the electrode lead that it is arranged in the atrium following implantation.

4. A pacing electrode arrangement according to claim 2, further comprising at least one additional electrode, located on the electrode lead at a first distance to the first pacing electrode and at a second distance to the second pacing electrode on the distal side.

5. A pacing electrode arrangement according to claim 4, wherein the additional electrode is designed as a sensing electrode.

6. A pacing electrode arrangement according to claim 4, further comprising means for selectively activating at least one of the first pacing electrode, the second pacing electrode and the at least one additional electrode.

7. A pacing electrode arrangement according to claim 6, wherein the means for selectively activating at least one of the first pacing electrode, the second pacing electrode and the at least one additional electrode activates those electrodes in one of alternative or joint combinations.

8. A pacing electrode arrangement according to claim 4, wherein the at least one additional electrode is arranged in the ventricle.

9. A pacing electrode arrangement according to claim 2, wherein the first pacing electrode is arranged on an electrode lead, which extends at least into the atrium and is designed to be floating.

10. A pacing electrode arrangement according to claim 1, wherein the first pacing electrode is one of shaped in such a way and connected to an electrode lead segment that is shaped in such a way that it occupies a predetermined position in the vena cava superior following implantation.

11. A pacing electrode arrangement according to claim 1, wherein the positioning means comprise means for adjusting a predetermined curvature of the electrode lead following implantation.

12. A pacing electrode arrangement according to claim 1, the positioning means include means that can be actuated from outside of the body for changing the position of at least one of the first pacing electrode and the second pacing electrode following implantation.

13. A pacing electrode arrangement according to claim 1, wherein at least one of the first pacing electrode and the second pacing electrode includes one of a ring-shaped and ring-segment shaped design with a maximum length/diameter ratio of 2.

14. A pacing electrode arrangement according to claim 13, wherein the one of a ring-shaped and ring-segment shaped designs have a length/diameter ratio of less than 1.

15. A pacing electrode arrangement according to claim 1, wherein at least one of the first pacing electrode and the second pacing electrode has a geometric surface area of less than 10 $mm^2$.

16. A pacing electrode arrangement according to claim 15, wherein at least one of the first pacing electrode and the second pacing electrode has a fractal surface microstructure for enlarging the electrically effective surface by a factor of at least $10^2$.

17. A pacing electrode arrangement according to claim 1, further comprising an extra-cardiac pacing electrode.

18. A pacing electrode arrangement according to claim 17, further comprising a pacemaker housing and wherein the extra-cardiac pacing electrode is incorporated as part of said pacemaker housing.

19. A pacing electrode arrangement according to claim 1, wherein the first pacing electrode and the second pacing electrode essentially enclose between them the sinus node of the of the cardiac stimulus generating and conduction system.

20. A pacing electrode arrangement according to claim 1, wherein the positioning means comprise at least one electrode lead component of shape-memory alloy which returns to a predetermined curvature following implantation.

* * * * *